US007014990B2

(12) United States Patent
Polyak et al.

(10) Patent No.: US 7,014,990 B2
(45) Date of Patent: Mar. 21, 2006

(54) MACHINE PERFUSION SOLUTION FOR ORGAN AND BIOLOGICAL TISSUE PRESERVATION

(75) Inventors: Maximilian Polyak, Glenmoore, PA (US); Ben O'Mar Arrington, 1116 Mount Tom Rd., East Stroudsburg, PA (US) 18301

(73) Assignee: Ben O'Mar Arrington, East Stroudsburg, PA (US)

( * ) Notice: Subject to any disclaimer, the term of this patent is extended or adjusted under 35 U.S.C. 154(b) by 0 days.

(21) Appl. No.: 09/976,805

(22) Filed: Oct. 12, 2001

(65) Prior Publication Data

US 2002/0068268 A1 Jun. 6, 2002

Related U.S. Application Data

(60) Provisional application No. 60/240,024, filed on Oct. 13, 2000.

(51) Int. Cl.
*A01N 1/00* (2006.01)

(52) U.S. Cl. ........................................ 435/1.1; 435/1.2

(58) Field of Classification Search .................... 435/2, 435/1.1, 1.2, 1.3
See application file for complete search history.

(56) References Cited

U.S. PATENT DOCUMENTS

| 4,798,824 A | 1/1989 | Belzer et al. |
| 4,879,283 A | 11/1989 | Belzer et al. |
| 4,994,367 A | 2/1991 | Bode et al. |
| 5,080,886 A | 1/1992 | Mickle et al. |
| 5,200,398 A | 4/1993 | Strasberg et al. |
| 5,370,989 A | 12/1994 | Koga et al. |
| 5,407,793 A | 4/1995 | Del Nido et al. |
| 5,498,427 A | 3/1996 | Menasche |
| 5,552,267 A | 9/1996 | Stern et al. |
| 5,693,462 A | 12/1997 | Raymond |
| 5,712,084 A * | 1/1998 | Osgood .................. 435/1.2 |
| 5,919,703 A | 7/1999 | Mullen et al. |

FOREIGN PATENT DOCUMENTS

| CN | 1178070 A | 4/1998 |
| JP | 06305901 | 11/1994 |
| WO | WO 96/03139 A1 | 2/1996 |

OTHER PUBLICATIONS

Fukuse et al., "Effects of Euro-Collins, University of Wisconsin, and New Extracellular-Type Trehalose-Containing Kyoto Solutions in an Ex Vivo Rat Lung Preservation Model", Transplantation 62 : 1212-17 (1996).*
Vargas et al., "Prostaglandin E1 Attenuation of Ischemic Renal Reperfusion Injury in the Rat", J. Amer. Coll. Surg. 180 (6) : 713-7 (1995).*

Polyak, M.M.R., et al., Calcium Ion Concentration of Machine Perfusate Predicts Early Graft Function in Expanded Criteria Donor Kidneys, 1999, Transplant International, 12(5):378-382.
Polyak, M., et al., Pulsatile Preservation Characteristics Predict Early Graft Function in Extended Criteria Donor Kidneys, 1997, Transplantation Proceedings 29:3582-3583.
Polyak, M., et al., The Influence of Pulsatile Preservation on Renal Transplantation in the 1990s, 2000, Transplantation 69:249-258.
Polyak, M., et al., Glutathione Supplementation During Cold Ischemia Does Not Confer Early Functional Advantage in Renal Transplantation, 1999, Transplantation, 70(1):202-205.
Polyak, M., et al., Supplemental Reduced Glutathione During Cold Ischemia Does Not Improve Early Renal Allograft Function, 2000, Transplantation Proceedings, 32:32-34.
Polyak, M., et al., Donor Treatment with Phentolamine Mesylate Improves Machine Preservation Dynamics and Early Renal Allograft Function, 1999, Transplantation, 69 (1):184-186.
Polyak, M., et al., The State of Renal Preservation for Transplantation in New York, 1999, Transplantation Proceedings, 31:2091-2093.
Polyak, M., et al., Prostaglandin E1 Influences Pulsatile Preservation Characteristics and Early Graft Function in Expanded Criteria Donor Kidneys, 1999, Journal of Surgical Research, 85:17-25.
Polyak, M., et al., Prostaglandin E1 Improves Pulsatile Preservation Characteristics and Early Graft Function in Expanded Criteria Donor Kidneys, 1998, ASAIO Journal 44:M610-M612.
Polyak, M., et al., Novel Preservation Solution Improves Early Function in the Cold Stored and Machine Preserved Kidney, 2001, American Journal Of Transplantation 1(1), Abstract #1330.
Sun, S.C., et al., Improved Recovery of Heart Transplants by Combined Use of Oxygen-Derived Free Radical Scavenges and Energy Enhancement, Journal of Thoracic and Cardiovascular Surgery, 1992, Issn 0022-5223, vol. 104, pp. 830-837, abstract only.
Le Gal Y.M., et al., Heart-Lung Protection from Ischemiuc Injury during 8 Hour Hypothermic Preservation, Acta Bio-Medica de L'Ateneo Parmense: Organo Della Societa di Medicina e Scienze Naturali di Parma, Italy, 1994, Issn 0392-4203, vol. 65, pp. 181-198, abstract only.
Hiromi, Wada, et al., Effective 30-hour Preservation of Canine Lungs with Modified ET-Kyoto Solution, Annals of Thorascic Surgery, 1996, Issn 0003-4975, vol. 61, pp. 1099-1105, abstract only.

* cited by examiner

*Primary Examiner*—Sandra E. Saucier
(74) *Attorney, Agent, or Firm*—Blank Rome LLP

(57) ABSTRACT

Machine perfusion solutions for the presentation of organs and biological tissues prior to implantation, including a prostaglandin having vasodilatory, membrane stabilizing, platelet aggregation prevention upon reperfusion, and complement activation inhibitory properties, a nitric oxide donor, a glutathione-forming agent, and an oxygen free radical scavenger.

12 Claims, No Drawings

MACHINE PERFUSION SOLUTION FOR ORGAN AND BIOLOGICAL TISSUE PRESERVATION

REFERENCE TO RELATED APPLICATION

This application claims the benefit of U.S. Provisional Application No. 60/240,024 filed on Oct. 13, 2000, entitled "Organ and Biological Tissue Preservation Machine Perfusion Solution," which is incorporated herein by reference.

FIELD OF INVENTION

The invention relates to the field of organ and biological tissue preservation. In particular, the invention relates to machine perfusion solutions for the preservation of organs and biological tissues for implant.

BACKGROUND OF INVENTION

It is believed that the ability to preserve human organs for a few days by cold storage after initial flushing with an intracellular electrolyte solution or by pulsatile perfusion with an electrolyte-protein solution has allowed sufficient time for histo-compatibility testing of donor and recipient. It is also believed that preservation by solution or perfusion has also allowed for organ sharing among transplant centers, careful preoperative preparation of the recipient, time for preliminary donor culture results to become available, and vascular repairs of the organ prior to implantation.

It is believed that the 1990's has been a decade characterized by increasing waiting times for cadaveric organs. In renal transplantation, the growing disparity between available donors and patients on the waiting list has stimulated efforts to maximize utilization of cadaveric organs. An obstacle that may arise in the effort to increase utilization is that maximal utilization may require transplantation of all available organs, including extended criteria donor organs. However, by extending the criteria for suitability of donor organs, transplant clinicians may risk a penalty with respect to graft function, diminishing the efficiency of organ utilization if transplanted organs exhibit inferior graft survival. Consequently, interventions that both improve graft function and improve the ability of clinicians to assess the donor organ may be crucial to achieving the goal of maximizing the efficiency of cadaveric transplantation.

The mechanisms of injuries sustained by the cadaveric renal allograft during pre-preservation, cold ischemic preservation and reperfusion are believed to be complex and not fully understood. However, it is believed that there exists ample evidence to suggest that many of the injurious mechanisms occur as a result of the combination of prolonged cold ischemia and reperfusion (I/R). Reperfusion alone may not be deleterious to the graft, since reperfusion after short periods of cold ischemia may be well-tolerated, but reperfusion may be necessary for the manifestation of injuries that originate during deep and prolonged hypothermia. It is suggested that four major components of I/R injury that affect the preserved renal allograft begin during cold ischemia and are expressed during reperfusion. These include endothelial injury, leukocyte sequestration, platelet adhesion and increased coagulation.

Hypothermically-induced injury to the endothelium during preservation may lead to drastic alterations in cytoskeletal and organelle structures. During ischemic stress, profound changes in endothelial cell calcium metabolism may occur. These changes may be marked by the release of calcium from intracellular depots and by the pathological influx of calcium through the plasma membrane. Hypothermic preservation may disrupt the membrane electrical potential gradient, resulting in ion redistribution and uncontrolled circulation of Ca++. The depletion of ATP stored during I/R may compromise ATP-dependent pumps that extrude Ca++ from the cell and the energy intensive shuttle of organelle membranes, causing a dramatic elevation of intracellular free Ca++.

Alterations in cytosolic Ca++ concentration may disrupt several intracellular functions, many of which may result in damaging effects. Unregulated calcium homeostasis has been implicated in the development of endothelial and parenchymal injury and is believed to be a fundamental step in the sequelae of steps leading to lethal cell injury. Among the most significant damaging effects of increased cytosolic Ca++ are believed to be the activation of phospholipase A1, 2 and C, the cytotoxic production of reactive oxygen species by macrophages, the activation of proteases that enhance the conversion of xanthine dehydrogenase to xanthine oxidase, and mitochondrial derangements.

Solutions for preserving organs are described in U.S. Pat. Nos. 4,798,824 and 4,879,283, the disclosures of which are incorporated herein in their entirety. Despite such solutions, it is believed that there remains a need for organ and tissue preserving solutions that allow for static storage and preservation, while demonstrating superior quality preservation of organ and tissue viability and function.

SUMMARY OF THE INVENTION

The invention provides an organ and tissue preserving solution for machine perfusion preservation that demonstrates superior quality preservation when compared to existing preserving media, in terms of organ and tissue viability and function. The organ and biological tissue preservation aqueous machine perfusion solution includes a prostaglandin having vasodilatory, membrane stabilizing, platelet aggregation prevention upon reperfusion, and complement activation inhibitory properties, a nitric oxide donor, and a glutathione-forming agent.

The invention also provides a preserved organ and biological tissue. The preserved organ and biological tissue includes a cadaveric organ or tissue within the machine perfusion solution in a deep hypothermic condition or a physiological condition.

The invention also provides a perfusion machine comprising a chamber that mimics a deep hypothermic environment or physiological environment, where the machine perfusion solution continuously circulates through the chamber.

The invention also provides a method for preserving an organ or biological tissue. The method includes pouring the machine perfusion solution into a chamber that mimics a deep hypothermic environment or physiological environment, circulating the machine perfusion solution continuously through the chamber, inserting a cadaveric organ or tissue into the chamber, and flushing the cadaveric organ or tissue with the machine perfusion solution.

The invention further provides a method of preparing an organ or biological tissue machine perfusion solution. This method includes providing a solution with sterile water, adding sodium gluconate, potassium phosphate, adenine, ribose, calcium chloride, pentastarch, magnesium gluconate, HEPES, glucose, mannitol, and insulin to the solution, and mixing prostaglandin E1, nitroglycerin and N-acetylcysteine into the solution.

DETAILED DESCRIPTION OF THE INVENTION

In accordance with the present invention, the organ and biological tissue preservation aqueous machine perfusion solution includes a prostaglandin having vasodilatory, membrane stabilizing, platelet aggregation prevention upon reperfusion, and complement activation inhibitory properties, a nitric oxide donor, and a glutathione-forming agent. The organ and biological tissue preservation machine perfusion solution is intended for infusion into the vasculature of cadaveric and living donor organs for transplantation. Once infused, the donor organs are exsanguinated and blood is replaced by the solution in the native vasculature of the organs to return the organs to a normothermic condition. The solution may be used under deep hypothermic conditions or physiological conditions. The solution remains in the vasculature of the organ as well as envelops the entire organ during the period of cold ischemia. This method of preservation allows for the extended storage of organs, tissues, and all biological substances. When the organ or tissue is returned to normothermic conditions, the solution is replaced with blood or other physiologic media. Variations of this solution may also be used for cold storage solution preservation. The machine perfusion solution of the invention may be used in the same manner and for the same tissues and organs as known machine perfusion solutions.

A machine perfusion solution of the invention includes a prostaglandin having vasodilatory, membrane stabilizing, platelet aggregation prevention upon reperfusion, and complement activation inhibitory properties. One such prostaglandin is Prostaglandin E1 (PGE1). PGE1 is an endogenous eicosanoid of the cyclooxygenase pathway and is utilized for its potent vasodilatory properties. In addition, PGE1 has cellular and organelle membrane stabilization properties, cryoprotective properties, and ability to prevent platelet aggregation upon the vascular endothelium post transplant. As such, PGE1 may inhibit neutrophil adhesion, inhibit neutrophil production of oxygen free radical species, counteract procoagulant activity after endothelial injury, and stabilize cell membranes. When used in vivo, PGE1 is metabolized almost instantaneously by first pass clearance through the lung, but during hypothermic conditions, PGE1 in the machine perfusion solution may remain vasoactive even after several hours.

A machine perfusion solution of the invention also contains a nitric oxide donor, such as nitroglycerin. Nitroglycerin is utilized in the solution because of its potent nitric oxide donation properties, its ability to dilate the venous vascular system and prevent vasospasm, and its ability to prevent complement activation upon transplant. Nitroglycerine is known to relax smooth muscle cells of the endothelium, scavenge free oxygen radicals during reperfusion, and prevent the production of such radicals during cold ischemia.

Compounds that form glutathione (glutathione-forming agents) are also components of a machine perfusion solution of the invention. One such compound is n-acetylcysteine. Glutathione (GSH) is synthesized from L-glutamate, L-cysteine, and glycine in 2 ATP-dependent reactions. The first reaction, known as catalyzed by gamma-glutamylcysteine synthetase, is effectively rate-limited by GSH feedback. The second involves GSH synthetase, which is not subject to feedback by GSH. When GSH is consumed and feedback inhibition is lost, availability of cysteine as a precursor becomes the rate-limiting factor. As such, N-acetylcysteine is proposed to be the only glutathione precursor that can enter the cell freely. In addition, the constitutive glutathione-building properties of N-acetylcysteine help prevent the formation of free oxygen radicals generated during the preservation period and during reperfusion with a recipient's blood.

According to a preferred embodiment of the invention, an organ and biological tissue preservation cold storage solution containing PGE1, nitroglycerin, and N-acetylcysteine in the preserving solution significantly improves vascular resistance, vascular flow, and calcium efflux during the organ preservation period. The inhibition of calcium efflux over time in kidneys preserved by the proposed solution suggests that, in addition to vasoactive effects, an additional cytoprotective and cryoprotective effect may also be important in ameliorating ischemic injury. These improvements are substantiated ultrastructurally by improved appearance of mitochondria in proximal tubular cells compared to mitochondria from kidneys not exposed to the proposed solution.

A machine perfusion solution of the invention may also contain components typically used in known machine perfusion solutions. See, U.S. Pat. Nos. 4,798,824 and 4,879,283. For example, other components that may be utilized in the solution include: sodium gluconate and Mg gluconate, which are impermeant anions that reduce cell swelling, $KH_2PO_4$, which provides acid-base buffering and maintains the pH of the solution, adenine, which is a precursor to ATP synthesis, and ribose, which reduces cell swelling during hypothermia. In addition, $CaCl_2$, which is a calcium-dependent mitochondrial function supplement, HEPES, which is an acid-base buffer, glucose, which is a simple sugar that reduces cell swelling and provides energy stores for metabolically stressed cell, and mannitol and pentastarch, which are oncotic supporters, may also be added. NaCl and KOH may also be used for acid-base buffering and maintenance of the pH of the machine perfusion solution.

In a preferred embodiment, the organ or biological tissue preservation machine perfusion solution includes, but is not limited to:

TABLE 1

| COMPOSITION | AMOUNT IN 1 LITER |
| --- | --- |
| Sodium Gluconate | 40–160 mM |
| $KH_2PO_4$ | 10–50 mM |
| Mg Gluconate | 1–15 mM |
| Adenine | 1–15 mM |
| Ribose | 1–15 mM |
| $CaCl_2$ | 0.1–2 mM |
| HEPES | 1–30 mM |
| Glucose | 1–30 mM |
| Mannitol | 10–100 mM |
| Pentastarch | 40–60 g/L |
| Prostaglandin E1 | 100–10,000 mcg/L |
| Nitroglycerin | 1–15 mg/L |
| N-Acetylcysteine | 0.1–5 mg/L |
| Sterile Water | 700–900 mL |

In a more preferred embodiment, the organ or biological tissue preservation machine perfusion solution includes, but is not limited to:

TABLE 2

| COMPOSITION | AMOUNT IN 1 LITER |
| --- | --- |
| Sodium Gluconate | 60–100 mM |
| $KH_2PO_4$ | 20–30 mM |
| Mg Gluconate | 3–8 mM |

TABLE 2-continued

| COMPOSITION | AMOUNT IN 1 LITER |
|---|---|
| Adenine | 3–8 mM |
| Ribose | 3–8 mM |
| CaCl$_2$ | 0.3–0.8 mM |
| HEPES | 8–15 mM |
| Glucose | 8–15 mM |
| Mannitol | 15–50 mM |
| Pentastarch | 45–55 g/L |
| Prostaglandin E1 | 250–2,500 mcg/L |
| Nitroglycerin | 3–8 mg/L |
| N-Acetylcysteine | 0.5–2 mg/L |
| Sterile Water | 700–900 mL |

In a most preferred embodiment, the organ or biological tissue preservation machine perfusion solution includes, but is not limited to:

TABLE 3

| COMPOSITION | AMOUNT IN 1 LITER |
|---|---|
| Sodium Gluconate | Approx 80 mM |
| KH$_2$PO$_4$ | Approx 25 mM |
| Mg Gluconate | Approx 5 mM |
| Adenine | Approx 5 mM |
| Ribose | Approx 5 mM |
| CaCl$_2$ | Approx 0.5 mM |
| HEPES | Approx 10 mM |
| Glucose | Approx 10 mM |
| Mannitol | Approx 30 mM |
| Pentastarch | Approx 50 g/L |
| Prostaglandin E1 | Approx 500 mcg/L |
| Nitroglycerin | Approx 5 mg/L |
| N-Acetylcysteine | Approx 1 mg/L |
| Sterile Water | Approx 800 mL |

A machine perfusion solution of the invention may be prepared by combining the components described above with sterile water, such as distilled and/or deionized water. For example, to prepare the solution, approximately 700–900 mL, or preferably about 800 mL, of sterile water is poured into a one liter beaker at approximately room temperature. Although a one liter beaker is used in this example, any other container of any size may be used to prepare the solution, where the component amounts would be adjusted accordingly. In the most preferred embodiment, the following are added, in any order, to the solution and each is mixed until dissolved in the solution: approximately 80 mol/L sodium gluconate, approximately 25 mol/L potassium phosphate, approximately 5 mol/L adenine, approximately 5 mol/L of ribose, approximately 0.5 mol/L of calcium chloride, and approximately 50 g modified pentastarch. The modified pentastarch is a fractionated colloid mixture of 40–60 kDaltons in diameter and is modified by infusing the pentastarch under 3 atm of pressure through a dialyzing filter with a bore size of about 40–60 kDaltons. About 5 mol/L magnesium gluconate, approximately 10 mol/L HEPES, approximately 10 mol/L glucose, and approximately 30 mol/L mannitol are also added, in any order, and mixed. Approximately 40 U of insulin is also added. Then, in a second step, approximately 1 mg of N-acetylcysteine, approximately 5 mg nitroglycerin, and approximately 500 mcg of modified prostaglandin E1 (PGE1) are added, in any order, to the solution. PGE1 is modified by centrifuging PGE1 under hypothermic conditions at 30K rpm and then filtering the resulting mixture through a 0.05 micro filter. The modified PGE1 has a half-life lengthened by a multiple of about 15. To adjust the pH of the solution to about 7.2–7.5, or preferably, 7.4+/–0.1, 5N KOH or NaOH is added, as needed. The first and second step may also be reversed.

The invention also provides a method for preserving an organ or biological tissue. The method includes pouring the machine perfusion solution into a chamber that mimics a deep hypothermic environment or physiological environment and moving the machine perfusion solution continuously through the chamber. The machine perfusion solution is infused in a mechanical fashion through the arterial or venous vascular system of cadaveric or living donor organs, or infused over or through an avascular biological substance in order to maintain organ or tissue viability during the ex vivo period. Preferred temperatures range from about 2–10° C. in the deep hypothermic condition and are about 37° C., or room temperature, in the physiological condition. Use of this solution provides for the serial assay of solution over time to determine hydrostatic and chemical changes. These hydrostatic and chemical changes provide a mechanism to determine the functional viability of the organ or tissue once it has been returned to physiologic conditions.

The invention further provides a perfusion machine comprising a chamber that mimics a deep hypothermic environment or physiological environment, where the machine perfusion solution continuously moves through the chamber. Any perfusion machine that is known in the art may be used with the solution, including machines providing pulsatile, low flow, high flow, and roller flow perfusion. Typically, the perfusion machine includes a unit for the static monitoring or transportation of organs or biological tissues and a cassette, or chamber, used to circulate perfusate through the organs or biological tissues. A monitor displays pulse pump rate, perfusate temperature, systolic, mean, and diastolic pressure, and real-time flow. Once such machine is the RM3 Renal Preservation System manufactured by Waters Instruments, Inc.® As discussed above, preferred temperatures range from about 2–10° C. in the deep hypothermic condition and are about 37° C., or room temperature, in the physiological condition.

The invention is further explained by the following of examples of the invention as well as comparison examples. In all of the examples, kidneys were procured from heart-beating donors and preserved in a laboratory by cold storage preservation. Randomization was accomplished as an open labeled, sequential analysis. All agents were added immediately prior to vascular flush.

Data Collected

The following donor, preservation, and postoperative recipient outcome data were collected for either Example 1 or Example 2: donor age (D age, years), final donor creatinine (D Cr, mg/dL), donor intraoperative urine output (U/O, mL), cold ischemic time (CIT, hours), perfusion time (PT, hours), perfusate [Na+] (mM/100 g), perfusate [Cl–] (mM/100 g), perfusate [K+] (mM/100 g), perfusate [Ca++] (mM/100 g), perfusate pH, renal flow during MP (FL, mL/min/100 g), renal resistance during MP (RES, mmHg/(mL/min/100 g), recipient age (R age, years), recipient discharge creatinine (R Cr, mg/dL), initial length of recipient hospital stay (LOS, days), immediate graft function (IF, %) defined as urine production exceeding 2000 mL during the first 24 post-operative hours, delayed renal allograft graft function (DGF, %) defined as the need for dialysis within the first 7 days post-transplant, and present function (3 Mo or 1 Yr., %) defined as 3 month or one year post-operative graft status.

Method of Preservation

Kidneys were perfused en bloc at 4° C. and at 60 beats per minute with either 1 liter of UW-MPS (Belzer-MPS, TransMed Corp., Elk River, Minn.), Belzer I-Albumin (Suny-Downstate, Brooklyn, N.Y.), or the Machine Perfusion Solution (Storage) (MPS) of the invention. The Belzer solution, which is also the Control-Belzer solution, is described in U.S. Pat. Nos. 4,798,824 and 4,879,283. The Albumin solution contained, per liter, 17.5 g sodium bicarbonate, 3.4 g potassium dihydrogen phosphate, 1.5 g glucose, 9 g glutathione, 1.3 g adenosine, 4.7 g HEPES, 200K units penicillin, 8 mg dexamethasone, 12 mg phenosulphathelein, 40 units insulin, 150 mL serum albumin, and 1 g magnesium sulfate. In each of the solutions, the kidneys were perfused on RM3 organ perfusion machines (Waters Instruments, Inc.®, Rochester, Minn.), which provide a fixed-pressure system that allows adjustment to the perfusion pressure, as needed. All kidneys were perfused at a systolic pressure below 60 mmHg. Perfusion characteristics (FL, RES, PT, [Na+], [Cl−], [K+], [Ca++], and pH) were measured when the kidneys were placed on the machine perfusion system, every 30 minutes for the first 2 hours of MP, and every hour thereafter throughout the period of MP. All chemical data were compared to a baseline assay of perfusate that had not circulated through the kidneys. All perfusion characteristics were standardized to 100 g of tissue weight.

Analysis

The following biochemical components of perfusate were measured every hour throughout MP with an Omni 4 Multianalyte system (Omni, AVL Medical Instruments, Atlanta, GA): [Na+], [Cl−], [K+], [Ca++], and pH. All biochemical assays were standardized to 100 g of tissue weight. For each measurement, a 0.5 cc aliquot of perfusate is drawn from the perfusion chamber, analyzed by the Omni, and is available for evaluation within 30 seconds.

Statistical analysis

All data are reported as mean values ±SEM unless otherwise noted. Paired and unpaired student's t-tests were used where appropriate. All statistical analyses were performed by Statview 4.5 software (Abacus Concepts, Berkeley, Calif.).

EXAMPLE 1

Comparison of selected donor, preservation, and outcome variables by method and type of preservation (mean +/− SEM)
n = number of recipients
ns = not significant

| Donor Characteristics | MPS (n = 82) (Embodiment of Table 3) | Belzer-MPS (n = 80) | p value (unpaired student's t-test) |
|---|---|---|---|
| Donor age (y) | 62.8 | 64.2 | ns |
| Final serum creatinine (mg/dl) | 1.2 | 1.1 | ns |
| Preservation characteristics | | | |
| Cold ischemic time (h) | 28 | 27 | ns |
| Outcome characteristics | | | |
| Delayed grant function (%) | 11 | 21 | 0.03 |
| 1 yr. function (%) | 95 | 95 | ns |

EXAMPLE 2

Comparison of selected donor, preservation, and outcome characteristics by method of machine perfusion solution (mean +/−SEM)
PGE1 = prostaglandin E1 (500 mcg/L)
NTG = Nitroglycerin (5 mg/L)

| | PGE1 (n = 152) | NTG (n = 50) | PGE1 + NTG (n = 48) (Embodiment of Table 3) | Control-Belzer-MPS (n = 140) | p value unpaired student's t-test |
|---|---|---|---|---|---|
| Donor Characteristics | | | | | |
| Donor age (y) | 41.1+/−6 | 44.3+/−5 | 42.2+/−9 | 44.1+/−5 | 0.72 |
| Final serum creatinine (mg/dl) | 1.0+/−0.2 | 1.2+/−0.3 | 0.9+/−02 | 0.8+/−0.5 | 0.45 |
| Intraoperative urine output (ml) | 240+/−80 | 220+/−90 | 300+/−100 | 240+/−60 | 0.56 |
| Preservation characteristics | | | | | |
| Cold ischemic time (h) | 24+/−4 | 23+/−4 | 22+/−6 | 23+/−4 | 0.61 |
| Perfusion time (h) | 17+/−3 | 19+/−6 | 15+/−8 | 16+/−5 | 0.33 |
| Outcome characteristics | | | | | |
| Immediate function (%) | 85+/−3 | 84+/−4 | 89+/−3 | 85+/−5 | |
| Delayed grant function (%) | 10+/−3 | 13+/−4 | 9+/−2 | 18+/−4 | |
| 3 month function (%) | 95+/−4 | 93+/−2 | 96+/−3 | 87+/−5 | |

While the invention has been disclosed with reference to certain preferred embodiments, numerous modifications, alterations, and changes to the described embodiments are possible without departing from the sphere and scope of the invention, as defined in the appended claims and their equivalents thereof. For example, although the detailed description may refer, at times, to only organs, the terms "organs" and "organ" encompass all organs, tissues, and body parts that may be transplanted. Accordingly, it is intended that the invention not be limited to the described embodiments, but that it have the full scope defined by the language of the following claims.

We claim:

1. The machine perfusion solution of claim 1 wherein the solution comprises about 1,000 micrograms/L prostaglandin E1, about 10 mg/L nitroglycerin, and about 0.2 mg/L N-acetylcysteine, further comprising:
   about 60–100 mM sodium gluconate;
   about 20–30 mM $KH_2PO_4$;
   about 3–8 mM magnesium gluconate;
   about 3–8 mM adenine;
   about 3–8 mM ribose;
   about 0.3–0.8 mM $CaCl_2$;
   about 8–15 mM HEPES;
   about 8–15 mM glucose;
   about 15–50 mM mannitol; and
   about 45–55 g/L pentastarch.

2. The machine perfusion solution of claim 1 wherein the solution comprises about 1,000 micrograms/L prostaglandin E1, about 10 mg/L nitroglycerin, and about 0.2 mg/L N-acetylcysteine, further comprising:
   about 80 mM sodium gluconate;
   about 25 mM $KH_2PO_4$;
   about 5 mM magnesium gluconate;
   about 5 mM adenine;
   about 5 mM ribose;
   about 0.5 mM $CaCl_2$;
   about 10 mM HEPES;
   about 10 mM glucose;
   about 30 mM mannitol; and
   about 50 g/L pentastarch.

3. The machine perfusion solution of claim 1 or 2 further comprising at least one of distilled water and deionized water.

4. An organ or biological tissue preservation aqueous machine perfusion solution comprising:
   about 1,000 micrograms/L prostaglandin E1;
   about 10 mg/L nitroglycerin;
   about 0.2 mg/L N-acetylcysteine;
   about 40–160 mM sodium gluconate;
   about 10–50 mM $KH_2PO_4$;
   about 1–15 mM magnesium gluconate;
   about 1–15 mM adenine;
   about 1–15 mM ribose;
   about 0.1–2 mM $CaCl_2$;
   about 1–30 mM HEPES;
   about 1–30 mM glucose;
   about 10–100 mM mannitol;
   about 40–60 g/L pentastarch; and
   about 700–900 mL sterile water.

5. A method for preserving a cadaveric organ or biological tissue, wherein the organ or tissue is a kidney or tissue from a kidney, comprising:
   pouring the machine perfusion solution of claim 1, 2, 3 or 4 into a chamber that mimics at least one of a deep hypothermic environment and physiological environment;
   circulating the machine perfusion solution continuously through the chamber;
   inserting the at least one of a cadaveric organ and tissue into the chamber; and
   flushing the at least one of a cadaveric organ and tissue with the machine perfusion solution.

6. The method of claim 5 wherein the flushing comprises:
   infusing the solution through vasculature of the at least one of a cadaveric organ and tissue.

7. The method of claim 5 wherein the flushing comprises:
   infusing the solution over or through an avascular biological substance of the at least one of a cadaveric organ and tissue to maintain viability during an ex vivo period.

8. The method of claim 5 further comprising:
   monitoring parameters of the at least one of a cadaveric organ and tissue.

9. The method of claim 5 further comprising:
   exsanguinating the at least one of a cadaveric organ and tissue; and
   replacing the machine perfusion solution with at least blood to return the at least one of a cadaveric organ and tissue to a normothermic condition.

10. A method of preparing an organ or biological tissue preservation machine perfusion solution of claim 1, 2, 3 or 4 comprising:
    providing a solution with sterile water;
    adding the sodium gluconate, potassium phosphate, adenine, ribose, calcium chloride, pentastarch, magnesium gluconate, HEPES, glucose, mannitol, and insulin to the solution; and
    mixing the prostaglandin E1, nitroglycerin and N-acetylcysteine into the solution.

11. The method of claim 10 further comprising:
    mixing the solution until all components are dissolved.

12. The method of claim 10 further comprising:
    infusing the pentastarch under pressure through a dialyzing filter;
    centrifuging the prostaglandin E1 under hypothermic conditions; and
    filtering the centrifuged prostaglandin E1.

* * * * *